United States Patent [19]

Herschler

[11] Patent Number: 4,568,547

[45] Date of Patent: * Feb. 4, 1986

[54] SOLID PHARMACEUTICAL COMPOSITIONS COMPRISING MSM AND THEIR PRODUCTION

[76] Inventor: Robert J. Herschler, 3080 NW. 8th Ave., Camas, Wash. 98607

[*] Notice: The portion of the term of this patent subsequent to Oct. 16, 2001 has been disclaimed.

[21] Appl. No.: 584,354

[22] Filed: Feb. 28, 1984

Related U.S. Application Data

[60] Continuation-in-part of Ser. No. 277,592, Jun. 26, 1981, Pat. No. 4,477,469, which is a division of Ser. No. 71,068, Aug. 30, 1979, Pat. No. 4,296,130, and Ser. No. 418,110, Sep. 14, 1982, Pat. No. 4,514,421.

[51] Int. Cl.$^4$ .................. A61K 31/17; A61K 31/10
[52] U.S. Cl. .................... 514/772; 264/117; 424/14; 424/16; 514/951; 514/960
[58] Field of Search ............... 264/117; 424/337, 14, 424/16, 357; 514/960

[56] References Cited

U.S. PATENT DOCUMENTS

| | | | |
|---|---|---|---|
| 3,234,091 | 2/1966 | Lang et al. | 424/14 |
| 3,546,339 | 12/1970 | Leeson et al. | 424/337 |
| 3,885,026 | 5/1975 | Heinemann et al. | 424/14 |
| 3,944,064 | 3/1976 | Bashaw et al. | 424/14 |
| 3,981,996 | 9/1976 | Leigh | 424/337 |
| 4,070,449 | 1/1978 | Rowsell et al. | 424/337 |
| 4,241,001 | 12/1980 | Lamond et al. | 264/117 |
| 4,294,819 | 10/1981 | Tencza | 424/16 |
| 4,296,104 | 10/1981 | Herschler | 424/337 |
| 4,296,130 | 10/1981 | Herschler | 424/337 |
| 4,447,421 | 5/1984 | Klothen | 264/117 |
| 4,477,469 | 10/1984 | Herschler | 424/322 |

*Primary Examiner*—Ronald W. Griffin
*Attorney, Agent, or Firm*—Millen & White

[57] ABSTRACT

Methylsulfonylmethane (MSM) is useful as a tableting and granulating aid for pharmaceutically active agents, especially those which are unstable in the presence of moisture, mixtures therewith being or formable into free-flowing powders or granules which are readily compressible into tablets of improved properties. A preferred method of forming such powders or granules involves mixing the pharmaceutically active agent under substantially anhydrous conditions with molten MSM or with particulate solid MSM at its softening point, cooling the resultant mixture and, when the MSM was molten, forming the solidified melt into granules or a free flowing powder and thereafter, if desired, compressing the powder or granules into tablets.

28 Claims, No Drawings

SOLID PHARMACEUTICAL COMPOSITIONS COMPRISING MSM AND THEIR PRODUCTION

BACKGROUND OF THE INVENTION

This invention relates to solid pharmaceutical compositions comprising methylsulfonylmethane as a tableting or granulation aid and to methods for their production. This is a continuation-in-part of application Ser. No. 277,592, now U.S. Pat. No. 4,477,469, filed June 26, 1981 as a divisional of application Ser. No. 071,068, filed Aug. 30, 1979, now U.S. Pat. No. 4,296,130; application Ser. No. 418,110, filed Sep. 14, 1982, now U.S. Pat. No. 4,514,421; and PCT Application US83/01396, filed Sep. 13, 1983.

Methylsulfonylmethane (MSM), also known as dimethylsulfone, is a well known chemical, m.p. 109°, $b.p._{760}$ 238°. Merck's Index (9th Ed.) describes it as being a high temperature solvent for many inorganic and organic substances. In U.S. Pat. No. 4,296,130, I disclose cosmetic and pharmaceutical preparations containing MSM for administration to the skin, nails, other tissue or body fluids. Although the patent is directed primarily to fluid compositions for topical use comprising MSM and the use of MSM as a blood diluent, I also disclose that it may take other forms, viz., solid or vapor, for administration by other routes, such as injection, inhalation, or oral ingestion and the like, and that it can be included in syrups, tablets or capsules which are ingested. In parent application Ser. No. 71,068, whose disclosure is incorporated herein by reference, I claim, inter alia, a method for altering the condition and/or body fluids of a subject by administering MSM thereto, a method for reducing brittleness of finger and toe nails by the topical administration of MSM thereto and a method for the purification of MSM. I disclose that MSM stabilizes certain substances such as carbamide (urea) so that the shelf life of certain cosmetic pharmaceutical preparations can be extended by the inclusion of MSM. As evidence thereof, I compare various aqueous gels containing only carbamide with corresponding gels also containing MSM.

In parent application Ser. No. 418,110, whose disclosure is incorporated herein by reference, I disclose that MSM is useful in relieving stress response symptoms which include gastrointestinal upset or inflammation of the mucous membrane, as well as being useful in treating a variety of other conditions and in one embodiment of the invention MSM is provided as a mixture of a gastrointestinal upset-promoting physiologically acceptable pharmaceutically active agent and MSM, e.g., in the form of tablets, capsules, dragees or pills.

In addition to the utilities for MSM disclosed by me in my above-cited patent and patent application, I have found that MSM facilitates the formation of pharmaceutically active agents into solid pharmaceutical forms, e.g., free flowing powders and granules, and into unit dosage solid forms, viz., tablets, capsules, dragees and pills.

It is well known that virtually all pharmaceutically active agents must be admixed with one or more pharmaceutically acceptable carriers or adjuvants in order to be formulated in a commercially acceptable manner into solid pharmaceutical dosage forms adapted for oral ingestion, either to impart thereto the requisite or desired physical properties to enable one to do so or to provide the bulk or volume required of such a form. A wide variety of sugars, starches, talc, monocalcium phosphate, calcium carbonate, etc., are used for such purposes. Each physical form requires specific processing and other characteristics. For example, powders and granules must be free flowing, non-hydroscopic, essentially colorless and, in order to minimize processing difficulties, resistant to acquisition of a static charge and to agglomeration. Granules additionally must be resistant to fracturing and powdering and, if they are to be formed into tablets, they must be compressible under conventional tableting conditions into commercially acceptable tablets. Tablets similarly must be resistant to fracturing and powdering, yet readily disintegratable in the stomach or, conversely, resistant to such disintegration if an active ingredient therein is unstable in the stomach.

I have found that such solid pharmaceutical compositions in which the pharmaceutical adjuvant or carrier consists essentially of MSM can readily, and with advantages over conventional adjuvants and carriers, be formulated employing conventional pharmaceutical formulating techniques. The resultant products often have surprisingly superior properties, compared to corresponding compositions employing conventional pharmaceutical adjuvants or carriers, especially those wherein the pharmaceutically active agent is storage unstable in the presence of moisture.

Accordingly, it is an object of this invention to provide novel solid pharmaceutical compositions in which MSM is an essential carrier or adjuvant. Another object is the provision of novel methods of formulating such compositions.

It is a further object of this invention to provide novel solid pharmaceutical compositions having improved properties. Another object is the provision of novel time release-sustaining medicaments which are effective for continuously releasing health and welfare active ingredients at a controlled rate of speed. Still another object is to provide solid solutions and dispersions demonstrating improved, delivery by reason of the physical state in the tablet matrix, including those with substantially improved gastric fluid solubilities. Still another object is to provide essentially water-free tablets employing novel binder and diluent which can serve alone as the tableting matrix or in combination with conventional adjuvants or carriers, for example, serving as the flow inducer of co-binders, such as starches and cellulose derived products, which cannot properly function without at least bound water and traces of free water. It is another object to impart stability and prolonged shelf life to pharmaceutical compositions in which a pharmaceutically active agent present therein is inherently water sensitive. Another object is to provide flexible methodology whereby tablets of gastric acid-sensitive health and welfare agents are protected while passing through the stomach for release in the more stable environment of the lower digestive tract, i.e., enteric tablets. Other objects will be apparent to those skilled in the art to which this invention pertains.

SUMMARY OF THE INVENTION

In a composition aspect, this invention relates to solid pharmaceutical compositions adapted for oral ingestion in the form of tablets, granules or a free-flowing powder and consisting essentially of an intimate, physical mixture of at least one dietary or pharmaceutically systemically active agent which is storage unstable in the presence of moisture and a pharmaceutically acceptable carrier therefor, wherein the mixture is substantially anhydrous, the carrier consists essentially of methylsulfonylmethane (MSM) and the pharmaceutically active agent is dissolved in the MSM or adheringly bonded to the surface of particles of the MSM.

In one process aspect, this invention relates to a pharmaceutical formulation method for producing a solid pharmaceutical composition in the form of tablets, granules or a free flowing powder, which comprises the steps of:

(a) admixing a pharmaceutically active compound, at a temperature from about 80° to about 110° C. at which it is stable, with (i) an amount of molten MSM effective to dissolve the former therein; or (ii) an amount of particulate solid MSM effective to adheringly bond the former thereto; and (b) cooling the resultant mixture to below its softening temperature and, when in Step a) the MSM was molten, reducing the solidified melt to particulate form and, optionally thereafter, compressing the thus-produced particulate form of the pharmaceutical composition into tablets.

In another process aspect, this invention relates to a pharmaceutical formulation process for producing a solid pharmaceutical composition adapted for oral ingestion which comprises the step of forming an intimate physical mixture of at least one pharmaceutically systemically active agent which is storage unstable in the presence of moisture and a pharmaceutically acceptable carrier therefor, into tablets, granules or a free-flowing powder, wherein the mixture is substantially anhydrous, the carrier consists essentially of methylsulfonylmethane (MSM) and the pharmaceutically active agent is dissolved therein or adheringly bonded thereto.

In a preferred aspect of each of these processes, the thus-produced product thereof are granules or a free-flowing powder which is thereafter compressed into ingestible tablets.

In another process aspect, this invention relates to a process for producing the compositions of this invention in particulate form which comprises condensing vaporized onto a moving bed of solid particles of a pharmaceutically active agent an amount of vaporized MSM effective to coat the surfaces of the particles.

DETAILED DISCUSSION

Methylsulfonylmethane (MSM) as a carrier or adjuvant in solid pharmaceutical compositions possesses highly desirable properties not heretofore found in any other suitable unit dosage pharmaceutical adjuvant, binder or filler. These properties, coupled with exceptionally low mammalian toxicity (it is a natural constituent of most fresh foods and beverages), ready availability and comparatively low cost, provides a highly desirable improvement to unit dosage pharmaceutical technology. Moreover, MSM is compatible with nearly all other known tableting excipients and active agents used in tablet and capsule forms, such as flavorants, dietary supplements and drugs. Because of its low melting point (109° C.), it is an exceptionally useful and safe solvent/-dispersant for most pharmaceutically active agents in unit dose form. When mixtures of such an agent and MSM at or above the softening temperature of MSM cool to ambient temperature, they can be processed with state of the art equipment to provide maximized uniformity of distribution of the pharmaceutically active agent or agents therein. A wide variety of instant, sustained, and delayed release tablets can be provided in which MSM serves as the binder or diluent. A further distinct advantage which MSM has over conventional binders, diluents and carriers, such as starches, cellulose esters and ethers, natural and synthetic gums and polymers of diverse compositions, is that it is readily available in a water-free state, which assures greater stability for a large number of active agents which are storage unstable in the presence of even trace quantities of water, particularly when subject to prolonged storage under adverse conditions. In addition, MSM permits new dry granulation methods, imparts special cohesive properties to compaction powders and desirable flow characteristics to filling compositions for capsules and tablet powders.

A wide variety of pharmaceutically systemically active agents can be formulated with MSM into storage stable solid pharmaceutical mixtures according to the processes of this invention, e.g., vitamins, minerals, amino acids, essential trace elements, hormones and antagonists thereof, steroids, non-steroid anti-inflammatory agents, antineoplastic agents, antigens, antihistaminic agents, neuropharmacologic agents, including analgesics, vasodilators, anticoagulants, antimicrobial agents, antiviral agents, antifungal agents, antiparasitic agents, heavy metal antagonists, locally active drugs moderating the digestive tract, such as enzymes, antacids, histamine antagonists, diuretics and cardiovascular drugs. Preferred are those agents which lose 1% or more, especially those which lose 5% or more, of their activity upon storage for 6 months in a hermetically sealed package at ambient temperature after formulation into a solid pharmaceutical form containing 0.5% or more by wt. of water, e.g., free-flowing powder, granules or tablets, dragees or pills.

The term "substantially anhydrous" as used herein means containing no more than 0.5% moisture, preferably less than 0.2%, and more preferably less than 0.1%. The term "consisting essentially of" as used herein means consisting at least 95% and preferably at least 97% by weight thereof. The term "storage unstable in the presence of moisture" means that in a conventionally packaged, hermetically sealed state, at least 1% of the activity of the pharmaceutically active agent is lost at ambient temperature in 6 months in solid pharmaceutical forms containing 0.5% or more by weight of moisture. The term "soluble in MSM" as used herein means dissoluble to the extent of at least 1%, preferably at least 5% by weight in MSM at the melting point of MSM. The term "adheringly bonded" means that the pharmaceutically active agent and the adjuvant therefor cannot be separated from each other by physical manipulation means. "Free-flowing powders", "granules" and "tablets" as used herein are used in their conventional pharmaceutical sense.

The weight ratio of MSM to the pharmaceutically active agent or agents in the solid compositions of this invention can vary widely, e.g., from about 100:1 to about 0.1:1, preferably about 1:1 to about 0.25:1.

Although the solid compositions of this invention consist essentially of MSM and one or more pharmaceutically systemically active agents, other conventional pharmaceutically acceptable adjuvants, fillers, flow-control or tableting agents can be present therein, preferably in minor amounts, e.g., up to about 5% by weight. Examples of such optionally present materials include inorganic salts, e.g., $CaCO_3$ and calcium mono-, di- and/or triphosphates, in amounts of 2% or more, e.g., 5% or more, and/or colloidal silica, e.g., 0.1% to about 2%.

The free-flowing powders of this invention have excellent physical and chemical characteristics, including good flow characteristics, resistance to the acquisition of static charge and compressibility into tablets of excellent properties.

The granulated pharmaceutical compositions of this invention have excellent physical and chemical properties as described hereinafter and can be used as such, filled into conventional ingestible tablets or compressed into tablets.

The use of MSM as the essential tableting aid, either alone or in combination with diverse other organic and inorganic, hydrophilic and hydrophobic excipients, provides tablets with useful and often superior properties, including excellent appearance, good resistance to fracturing and powdering and ready dissolution in the stomach.

In the generic process aspect of this invention, an ultimate physical mixture consisting essentially of one or more pharmaceutically systemically active agents, preferably those which are unstable to moisture, and MSM as an adjuvant or carrier therefor, is formed while the MSM is at its softening point, i.e., about 80°–108° C., while it is molten or while it is in vapor form.

In a preferred form, a substantially anhydrous mixture thereof is formed by mixing a moving bed of the pharmaceutically active agent or agents in particulate form with particulate MSM at its softening temperature so that the former is adheringly bonded to the surface of the latter, and thereafter cooling. Depending on the conditions employed, the resulting mixture is produced as a free-flowing powder or granules.

In another preferred aspect, the pharmaceutically active agent or agents, preferably in substantially anhydrous form, is dissolved in molten MSM, which also is substantially anhydrous. If the mixture is not substantially anhydrous, it can be rendered so by placing the molten mixture under a vacuum until the free water therein is removed. The molten mixture is then cooled to below the softening temperature of the MSM, preferably to ambient temperature, and the solidified melt is thereafter broken up into granules and/or a free-flowing powder.

In another preferred process aspect, volatilized MSM is condensed onto a moving bed of the pharmaceutically active agent or agents in particulate form. This can be done at ambient pressure or preferably at reduced pressure, e.g., 20 to <1 mm Hg. In this aspect also, both the MSM and the pharmaceutically active agent are substantially anhydrous. If the starting MSM is not anhydrous, it can be rendered so by heating, e.g., by microwaves or by conventional heating under a vacuum. If more than a trace of water is present, a solution results which recrystallizes as the water is removed. One can quickly obtain an accurate estimate of the water content of MSM by measuring its temperature increase upon microwave induction under standard conditions. For reproducible results, one should use a sample size of at least 10–15 grams. It was found that the other components, separately or in admixture with the MSM could also be dried by this procedure.

GRANULATION

In the granulating process aspect of this invention, MSM is intimately mixed with one or more pharmaceutically active agents as defined herein to form the mixture into granules. Preferably, this is accomplished by the steps of:

(a) admixing a pharmaceutically active compound at a temperature from about 80° to about 110° C. at which it is stable, with (i) an amount of molten MSM effective to dissolve the former therein; or (ii) an amount of particulate solid MSM effective to adheringly bond the former thereto; and (b) cooling the resultant mixture to below its softening temperature and, when in Step a) the MSM was molten, reducing the solidified melt to granules.

In another granulation process aspect, vaporized anhydrous MSM is condensed onto particles of the pharmaceutically active agent or of a mixture thereof and a conventional excipient.

The granules thus-formed have excellent properties including compressibility into tablets which also have excellent properties as described hereinafter; high resistance to fracturing and powdering; resistance to the acquisition of a static charge; excellent release rate of the pharmaceutically active agent therein into stomach fluids; extremely low hydroscopicity; good flow characteristics and resistance to caking and sticking to processing equipment during conventional manufacturing steps, such as filling into capsules or compression into tablets; and generally superior physical and processing characteristics.

Drying, if avoidable, is desirable by reason of cost, time savings and oftentimes the inherent increased stability of active ingredients demonstrating instability in the presence of moisture. In wet granulation, it is common practice to form a paste of the tablet ingredients, usually employing water or aqueous organic solvent, followed by drying, then pulverization of the thus-formed dry cake into granules of uniform size and/or a free-flowing powder. In conventional methodology for dry granulation, dry powders are mixed, compressed into slugs, crushed and screened before batching and processing into capsules or tablets. MSM has unique advantages an an excipient in both types of granulation techniques. MSM is commercially available in sizes from massive crystals over an inch or two in length to micronized powders passing through all but the finest mesh screens. By employing MSM as the essential granulation excipient, aqueous liquids can be avoided and the dry granulation batch is merely heated to usually 80-110° C. with constant mixing. The pharmaceutically active agent or agents and other desired excipients dissolve in or disperse onto the MSM matrix, to form a substantially anhydrous product which is readily processed to desired specifications with conventional equipment. Not only is the pharmaceutically active agent better distributed in the matrix, several separate manufacturing steps can be eliminated.

PHYSICAL INTEGRITY

Although considered bad manufacturing and packaging practice, pharmaceutical tablets are sometimes bulk packed in large, deep draft containers and shipped long distances, with the result that the lower layer of tablets is subject to physical stress sufficient to crush or fragment some of the tablets. The parameter of physical integrity can be conveniently measured by imposing the weight of a free-moving 2.5 kg rod on the face of a tablet resting on a fixed, smooth, hard surface. Most tablets are crushed by this test, including tablets employing MSM as the only binder or diluent. Modifiers such as fatty acids and alcohols, their esters, beeswax, starches and cellulose esters and ether generally have little if any beneficial effects on the physical integrity of tablets in this test. In fact, those agents with lubricant properties tended to diminish the physical integrity. Unexpectedly, it was found that the presence of about 2% by wt. and preferably at least 5% by wt. of any of several inorganic salts, such as calcium carbonate, mono-, di- or tricalcium phosphate, greatly reinforced tablets which employ MSM as the essential binder.

HYGROSCOPICITY

Water generally is an undesired yet unavoidable component of most organic tableting binders and diluents, such as sugars, starches, cellulose ester and ethers. These agents also tend to attract water, i.e., exhibit hygroscopicity. Many drugs otherwise suited for unit dosage preparation are storage unstable in the presence of even trace quantities of water. Aspirin is one of many examples of drugs subject to hydrolysis. Not only can MSM be provided essentially free of all water, but another unique property is the very low attraction MSM has for water. For example, a 10 gram sample of dried MSM placed on a watch glass over a container of water enclosed in a bell jar for 24 hours exhibits a weight gain of only about 0.01 gram.

COMPOSITIONS WITH IMPROVED FLOW PROPERTIES

Although pulverized and microcrystalline forms of dry MSM have good flow properties, their flow properties are significantly improved by the presence therein of from about 0.25–2% by weight of fumed or colloidal silica, particularly where traces of moisture remain in the MSM.

CAPSULE AND TABLET DOSAGE FORMS

MSM is exceptionally suited when pre-granulation is employed in the production of tablets and capsules. An unique feature of MSM is its ability to vaporize and colloidally disperse (seemingly sublime) even below its usual melting point of about 109° C. MSM, whether introduced under ambient or vacuum conditions, readily coats particulate pharmaceutically active agents and penetrates and permeates any available porous structure. In tableting, MSM therefore can be introduced at any point along the production line, even at the lubricant addition point, which often is the last stage prior to compaction. MSM does not itself induce undesired bridging in the hoppers and feed frames. Vapor granulation procedures are thus facilitated by including MSM.

MSM is compatible with most other diluents, binders, glidants as well as lubricants, disintegrants and colorants (two exceptions are mineral oils and paraffin waxes but waxes of vegetable orgin are generally compatible). Tablets whose carrier and adjuvant is predominantly MSM are readily coated with state of the art materials and methods. MSM is also compatible with virtually all pharmaceutically active agents which can be formulated into solid unit dosage forms.

In marked contrast with conventional diluents and binders, MSM is also an exceptional solvent for many pharmaceutically active agents which are virtually insoluble in the relatively few solvents suitable for use in granulation procedures. In the present state of the art, water is the most commonly used solvent, which requires removal before forming unitized dosage forms. MSM solutions are generally ambient friable solids. It is therefore possible to prepare unitized dosage forms with unique and highly desirable properties. For example, the broad spectrum anthelmintic and fungicide 2-(4-thiazolyl)benzimidaxole is illustrative of MSM's uniqueness. This compound, though reasonably soluble in the mammalian-toxic solvent dimethyl formamide, is only slightly soluble in ether, esters, alcohols and halogenated solvents. A solution of one gram of 2-(4-thiazolyl)benzimidazole in nine grams of molten MSM when allowed to cool to ambient temperature possesses a bright yellow color in crystalline form and can be readily reduced to a flowable powder. This powder can readily be recompressed into tablets. The powder is useful as a binder of itself and is compatible with a wide variety of conventional tablet matrixes and can even be used as such to fill capsules. Of special interest is the fact that such solid solutions readily disperse in water or gastric solution at 37° C. and hence are almost instantly available for gut absorption following ingestion. It is thus apparent that MSM is a unique excipient of exceptional value in unit dose technology where highly desirable homogeneity and thus uniformity of distribution is readily obtained. These qualities, coupled with the increased surface area for the active agent and the enhanced tablet disintegration rate imparted by the MSM, assures enhanced absorption and systemic uptake.

Although it is possible to prepare MSM unit dosage forms that rapidly disintegrate for rapid absorption, it is also possible, because of the unique characteristics of MSM, to prepare time-release forms by incorporating conventional tableting excipients known to produce time delay effects.

Certain pharmaceutically active agents must be protected from gastric acids. Penicillin G is illustrative of such chemically sensitive compounds. By controlling release rate of the unit dosage form, the pharmaceutically active agent is allowed to pass safely through the gut and into the more favorable environment of the small intestine.

Pulverized and microcrystalline forms of dry MSM have good flow properties and therefore hopper bridging and other production problems are generally avoided using MSM as the only excipient. However, flow properties are significantly improved with fumed or colloidal silica, particularly where traces of moisture remain in the MSM. Significant improvement is seen in compositions employing as excipient a mixture of from 98% to 99.75% MSM powder and from 0.25% to 2% colloidal silica (weight basis). Although larger proportions of silica can be used, flow is not greatly improved above about the 2% by weight level. Flow properties are easily measured by allowing a measured amount of a test sample to flow from a funnel to a flat, smooth surface. Any test sample cleanly flowing from the funnel and flattening out on the smooth surface, i.e., acting fluid-like, will pass freely to the die cavities of automatic tableting machines thereby avoiding costly delays, production losses and off-grade products.

DRYING ADVANTAGES

Pharmaceutically active agents, alone or in combination with excipients which are soluble or commercially isolated from water solution, can be conveniently combined with MSM as a solution thereof before spray or other drying procedure to yield a pre-tableting concentrate in which the pharmaceutically active agent is distributed therein to the optimum degree. The advantages over dry blending are obvious and set MSM apart from other unitized dosage binder-diluent agents, such as cellulose ester and ethers, starches, inorganic salts, such as calcium carbonate and other agents of the present art.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

All percentages and parts are by weight and temperatures are degrees centigrade.

EXAMPLE I

Comparison of MSM and amylose as tableting binders

Tablet binder grade commercial amylose which contains 10–14% by wt. water as a normal constituent was compared with dry powdered pharmaceutical grade MSM containing less than 0.1% water as the tableting binder for ascorbic acid, which is difficult to compress directly into tablets without binder and is unstable in the presence of water. The tableting formulations were:

|  | Formula A | Formula B |
| --- | --- | --- |
| Ascorbic acid | 50% | 50% |
| Amylose | 48% | — |
| MSM | — | 48% |
| Stearic acid | 2% | 2% |

Formulation B was dried by microwave induction in a standard household microwave oven.

Tablet hardness and friability were determined for 10 tablets from each formula. Formula A averaged 5.4 kg. hardness whereas Formula B averaged 5.9 kg. Friability of the two formulae as determined by employing a Roche friabulator was essentially the same.

It was not possible to form acceptable tablets with the amylose of Formula A which had been vacuum dried 12 hours at 50° and at 5 mm Hg to a moisture content of 9.8% by wt., because the tablets had too low a binding strength.

EXAMPLE II

Vapor phase granulation binder coating

The contents of two Pyrex round-bottom flasks with 24/40 fitted necks were dried in a rotary vacuum evaporator using heating from an external infrared lamp and vacuum to about 25 mm Hg. Flask 1 contained 50 grams of MSM which had a water content of between 2–3% before drying. Flask 2 contained, in particulate form, an intimate physical mixture of 50 grams of ascorbic acid, 5 grams of potassium bicarbonate, 5 grams of alginic acid, 5 grams of glycine and 2 grams of magnesium stearate, with an unknown moisture content prior to drying.

After drying the contents of both flasks to a moisture content of 0.1% (max.), the two flasks were interconnected using a fitted 24/40 connector and arranged to slowly rotate with the connector in the horizontal position. The flask containing the dry ascorbic acid and excipients was unheated. The flask containing the MSM was heated with two infrared lamps until vaporization by sublimation occurred. The MSM passed in the gaseous phase to the cool flask containing the ascorbic acid mixture, where it precipitated, forming a coating of the particulate or granular mixture. Eventually all the MSM was transferred to Flask 2, forming a coating on the ascorbic acid mixture. This coated mixture was cooled to ambient temperature and then pulverized to a free-flowing powder in a mortar passing through a 1/16 inch sieve. The screened powder was compressed directly into excellent tablets containing 250 mg. of Vitamin C per unit. This novel technique is efficient and effective and provides essentially anhydrous and therefore stable tableting feed stock.

TABLETING WITH MSM

In the following pilot commercial tableting runs, MSM was employed as the tablet binder (quantities are per tablet) using a Stokes BB-2, double rotary, tablet press with 25 stations, i.e., makes 25 tablets/compression, or comparable convention commercial tableting machinery, was used to form the tablets. In these pilot runs, several commercial practices were first employed and then eliminated without loss of tablet quality and with a gain in production ease and economy. As an essential step, the final combination of all ingredients were milled to assure a homogenous mixture of the active ingredients and the MSM and to provide a proper particulate size assuring good flow to the press. Mixtures of water insensitive ingredients, such as magnesium oxide, zinc oxide, manganese and selenium chelates and ferrous fumarate, with MSM were prepared as a water-wetted granulation cake, which was dried on trays using conventional circulating heated air. Water sensitive substances, for example, Vitamin C and amino acids, were mixed with MSM using alcohol (ethanol or isopropanol) to prepare the granulation cake. After drying, all granulation cakes were disintegrated, blended with the other ingredients and finally milled and screened.

EXAMPLE III

| Ingredients* | Amount |
| --- | --- |
| Beta carotene | 5000 IU |
| Vitamin E | 15 IU |
| Vitamin C | 250 mg |
| Niacin | 10 mg |
| Bioflavonoids | 5 mg |
| Magnesium | 50 mg |
| Zinc | 15 mg |
| Iron | 5 mg |
| Selenium | 15 mcg |
| Manganese | 1 mg |
| MSM | 250 mg |

*Ingredients: Vitamin C (ascorbic acid, calcium ascorbate, sodium ascorbate), magnesium oxide, potassium bicarbonate, beta-carotene, dl-alpha tocopheryl acetate, zinc oxide, ferrous fumarate, niacin, manganese chelate, selenium chelate, glycine, aspartic and glutamic acid HCl, bioflavonoids, magnesium stearate.

EXAMPLE IV

| Ingredient* | Amount |
| --- | --- |
| Vitamin C | 60 mg |
| Vitamin $B_1$ | 2.1 mg |
| Vitamin $B_2$ | 2.4 mg |
| Vitamin $B_6$ | 2 mg |
| Vitamin $B_{12}$ | 18 mcg |
| Niacin | 20 mg |
| Pantothenic acid | 10 mg |
| Folic acid | 400 mcg |
| Magnesium | 125 mg |
| Zinc | 15 mg |
| Tryptophan | 25 mg |

-continued

| Ingredient* | Amount |
|---|---|
| MSM | 250 mg |

*Ingredients: magnesium oxide, ascorbic acid, tryptophan, potassium bicarbonate, niacin zinc oxide, d-calcium pantothenate, glycine, lysine, and aspartic acid, glutamic acid HCl, folic acid, riboflavin, thiamine mononitrate, pyridoxine HCl, magnesiumstearate, Vitamin $B_{12}$.

EXAMPLE V

| Ingredient* | Amount |
|---|---|
| Vitamin A | 5000 IU |
| Vitamin D | 100 IU |
| Vitamin E | 30 IU |
| Vitamin C | 60 mg |
| Biotin | 30 mcg |
| Pantothenic acid | 10 mg |
| Magnesium | 100 mg |
| Tryptophan | 25 mg |
| MSM | 250 mg |

*Ingredients: magnesium oxide, methyl-sulfonylmethane (MSM), ascorbic acid, dl-alpha tocopheryl acetate, tryptophan, potassium bicarbonate, d-calcium pantothenate, vitamin A acetate, sodium ascorbate, calcium ascorbate, glycine, lysine and aspartic acid, glutamic acid HCl, magnesium stearate, biotin, vitamin $D_3$.

EXAMPLE VI

| Ingredient* | Amount |
|---|---|
| Beta-carotene | 1000 IU |
| Vitamin C | 60 mg |
| Vitamin $B_1$ | 2.1 mg |
| Vitamin $B_2$ | 2.1 mg |
| Vitamin $B_6$ | 2.0 mg |
| Vitamin $B_{12}$ | 18 mcg |
| Niacin | 20 mg |
| Pantothenic acid | 10 mg |
| Folic acid | 400 mcg |
| Magnesium | 127 mg |
| Zinc | 10 mg |
| Lysine | 5 mg |
| Cystine | 5 mg |
| Phosphatidylcholine | 10 mg |
| dl-carnitine | 10 mg |
| Mucopolysaccharide complex | 10 mg |
| Liver concentrate containing naturally occurring factors of superoxide dismutase | 625 units |
| Catalase | 12000 units |
| Glutathione peroxidase | 900 units |
| MSM | 250 mg |

*Ingredients: magnesium oxide, ascorbic acid, liver conc., phosphatidyl lecithin, potassium bicarbonate, niacin, zinc oxide, d-calcium pantothenate, bovine cartilaginous tissue, dl-carnitine, beta-corotene, aspartic acid, glutamic acid HCl, glycine, cystine, lysine HCl, folic acid, riboflavin, thiamine mononitrate, pyridoxine HCl, Vitamin $B_{12}$.

These pilot studies demonstrated two important factors concerning the use of MSM as a tablet binder:

1. MSM was entirely compatible with the state of the art methodology for preparing tablet-form dose units.
2. With MSM as the binder, where proper dry milling preceded compression, the labor intensive steps required in preparing granulation cake could be eliminated. MSM has a unique and novel role in tableting, since it wets and binds to conventional dry tablet ingredients under temperature and pressure. This flow and wetting property can avoid the necessity of wet granulation without compromising tablet quality.

EXAMPLE VII

Dry Granulation

Magnesium generally is a desired element in dietary supplements. Magnesium oxide is one source thereof which is commonly employed and also serves further as a dry diluent. 100 grams of magnesium oxide was combined with 150 grams of dry MSM. Blending included grinding the mixture in a mortar. The combination was then placed in a large mouth pyrex vessel, closed with aluminum foil and heated to about 105°-110° C. A solid cake formed which appeared to be a uniform dispersion of magnesium oxide in MSM when examined under a low power microscope. The cake could be easily milled and is an excellent binder in tablet formulations.

EXAMPLE VIII

Free-Flowing Powder

One gram of 2-(4-thiazolyl)benzimidazole, a broad spectrum anthelmintic and fungicide is dissolved in nine grams of molten MSM, cooled to ambient temperature and then reduced to a powder in a conventional manner. The powder is free-flowing and can be recompressed into tablets or filled into capsules. The solid solution readily disperses in water or gastric solution at 37° and hence is almost instantly available for gut absorption following ingestion.

EXAMPLE IX

Timed Release Tablets

A tablet formed from 250 mg of MSM, 250 mg of vitamin C, 25 mg of potassium bicarbonate, 20 mg of glycine and 10 mg of magnesium stearate will totally disintegrate in simulated gastric fluid after less than 15 minutes. By adding various state of the art tableting and granulation excipients, e.g., C-10 to C-18 fatty acids and fatty alcohols, polyvinyl alcohol, rosin, dl-pantothenyl alcohol, cellulose esters and ethers, polyvinyl acetate, starches, beeswax and calcium carbonate, it is possible to regulate disintegration over a period of at least ten hours.

EXAMPLE X

A tablet formed from 200 mg of MSM, 200 mg of vitamin C, 10 mg glycine, 10 mg magnesium stearate, 5 mg polyvinyl acetate, 5 mg hydroxypropyl methyl cellulose, 10 mg stearic acid and 10 mg of cetyl alcohol uniformly disintegrated in simulated gastric fluid over a five hour period after which period total disintegration was observed.

EXAMPLE XI

A tablet containing 100 mg of MSM, 25 mg potassium penicillin G (or other active agents which must be protected from gastric acids), 10 mg glycine, 10 mg calcium stearate, 30 mg starch, 15 mg cetyl alcohol and 15 mg of hydrogenated rosin released 65% of the K penicillin G by hour 6 and 95% by hour 10. In this preparation, a melt of the MSM and hydrogenated rosin was solidified to form a solid solution and micronized prior to blending with the other ingredients. By controlling the release rate of the unit dosage form, the active agent can pass safely through the stomach and into the more favorable environment for adsorption of the small intestine.

EXAMPLE XII

The effect of MSM on bioavailability of a pharmaceutical compound, viz., aspirin, was determined using commercial 5 grain aspirin tablets (Bayer ®) and tablets formed from 5 grains (0.324 grams) of calcium acetylsalicylate, 0.0314 grams potassium bicarbonate, 0.0026 grams magnesium stearate and 0.290 grams MSM (milled powder containing 2% by weight of a food and drug grade colloidal silica). Four tablets of either the commercial or test aspirin product were combined in ground meat and fed to 12-hour starved mongrel dogs. Blood was drawn from each dog at 5 minute intervals during the first 0.5 hour and at 15 minute intervals thereafter. The peak blood level with the commercial aspirin occurred at 20 minutes, while the peak level with the test tablets was at 15 minutes. The commercial aspirin could not be detected in the 2.5 hour blood samples, whereas the test tablets provided an analyzable concentration of aspirin in the blood at 3.0 hours post administration.

BIOAVAILABILITY

EXAMPLE XIII

To determine the effect of MSM on the bioavailability of a pharmaceutically active agent, aspirin tablets in which MSM was the tableting excipient were compared with commercial (Bayer) 5 grain aspirin tablets. The MSM test tablets 0.324 grams (5 grains) were prepared by compressing into tablets (hardness) a free-flowing powder consisting (per tablet) of calcium acetylsalicylate, 0.290 grams MSM, 0.0314 grams potassium bicarbonate and 0.0026 grams magnesium stearate. The MSM used was a milled powder containing 2% by wt. of a food and drug grade colloidal silica product. The free-flowing powder was prepared by use of a laboratory mill.

Four tablets of either the commercial (Bayer) or MSM test aspirin were combined in ground meat and fed to 12-hour starved mongrel dogs. Bloods were drawn at 5-minute intervals during the first 0.5 hour and at 15 minute intervals thereafter. The peak blood level with the commercial aspirin composition occurred at 20 minutes, whereas the peak level with the MSM test composition occurred at 15 minutes, indicating faster systemic uptake with the MSM content tablets. Of possible therapeutic interest was the finding that commercial aspirin was undetected in the 2.5 hour blood samples, while the MSM content test tablets provided an analyzable concentration in the blood at 3.0 hours post administration. This suggests that MSM as a tablet binder and diluent allows rapid uptake of an active agent and may provide prolonged systemic aspirin availability.

TIME RELEASE UNIT DOSAGE FORM

EXAMPLE XIV

A tablet formed of 250 mg of MSM, 250 mg of vitamin C, 25 mg of potassium bicarbonate, 20 mg of glycine and 10 mg of magnesium stearate will totally disintegrate in simulated gastric fluid in less than 15 minutes. By adding conventional tableting and granulation excipients. e.g., C-10 to C-18 fatty acids and fatty alcohols, polyvinyl alcohol, rosin, dl-pantothenyl alcohol, cellulose esters and ethers, polyvinyl acetate, starches, beeswax and calcium carbonate, it is possible to regulate disintegration over a period of at least 10 hours.

EXAMPLE XV

A tablet formed from an intimate mixture of 200 mg of MSM, 200 mg of vitamin C, 10 mg glycine, 10 mg magnesium stearate, 5 mg polyvinyl acetate, 5 mg hydroxypropyl methyl cellulose, 10 mg stearic acid and 10 mg of cetyl alcohol uniformly disintegrated in simulated gastric fluid over a 5 hour period, after which total disintegration occurred.

EXAMPLE XVI

A tablet formed from 100 mg of MSM, 25 mg potassium penicillin G, 10 mg glycine, 10 mg calcium stearate, 30 mg starch, 15 mg cetyl alcohol and 15 mg of hydrogenated rosin released 65% of the K penicillin G in 6 hours and 95% in 10 hours after ingestion. The MSM and hydrogenated rosin were first combined as a solid solution and micronized prior to blending with the other agents.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a solid pharmaceutical composition adapted for oral ingestion, in the form of tablets, granules or a free-flowing powder and consisting essentially of an intimate, physical mixture of at least one pharmaceutically systemically active agent which is storage unstable in the presence of moisture and a pharmaceutically acceptable carrier therefor, the improvement wherein the mixture is substantially anhydrous, the carrier consists essentially of methylsulfonylmethane (MSM) and the pharmaceutically active agent is dissolved in the MSM or adheringly bonded to the surface of particles of the MSM.

2. A composition according to claim 1, wherein the carrier consists of at least 95% by weight of MSM.

3. A composition according to claim 1, in the form of a free-flowing powder.

4. A composition according to claim 1, in the form of granules.

5. A composition according to claim 1, in the form of tablets.

6. Tablets according to the composition of claim 5, wherein the pharmaceutically active agent is aspirin.

7. Tablets according to the composition of claim 5, wherein the pharmaceutically active agent comprises one or more vitamins.

8. A composition according to claim 1, wherein the carrier comprises up to 5% by weight thereof of at least one of colloidal or fumed silica, calcium carbonate and calcium mono-, di- or triphosphate.

9. A composition according to claim 1 in the form of tablets, wherein the carrier consists of at least 95% by weight of MSM.

10. A pharmaceutical formulation method for producing a solid pharmaceutical composition in the form of tablets, granules or a free-flowing powder, which comprises the steps of:

(a) admixing a pharmaceutically active compound at a temperature from about 80° to about 110° C. at which it is stable, with
  (i) an amount of molten MSM effective to dissolve the former therein; or
  (ii) an amount of particulate solid MSM effective to adheringly bond the former thereto; and
(b) cooling the resultant mixture to below its softening temperature and, when in Step a) the MSM was molten, reducing the solidified melt to particulate form.

11. A method according to claim 10, wherein in Step a) both the MSM and the pharmaceutically active agent are in solid particulate form.

12. A method according to claim 11, comprising the further step of filling the thus-produced particulate form into capsules or compressing the thus produced particulate form into tablets.

13. A method according to claim 10, wherein in Step (a), the MSM is molten.

14. A method according to claim 13, wherein in Step (b) the solidified melt is formed into granules.

15. A method according to claim 13, wherein in Step (b), the solidified melt is formed into a free-flowing powder.

16. A method according to claim 14 comprising the further step of compressing the thus-produced granules into tablets.

17. A method according to claim 15 comprising the further step of filling the thus-produced powder into ingestible capsules or compressing the thus-produced powder into ingestible tablets.

18. A method according to claim 10, wherein the carrier comprises up to 5% by weight of at least one of colloidal or fumed silica, calcium carbonate and calcium mono-, di- or triphosphate.

19. In a pharmaceutical formulation method for producing a solid pharmaceutical composition adapted for oral ingestion which comprises the step of forming an intimate physical mixture of at least one pharmaceutically systemically active agent which is storage unstable in the presence of moisture and a pharmaceutically acceptable carrier therefor, into tablets, granules or a free-flowing powder, the improvement wherein the mixture is substantially anhydrous, the carrier consists essentially of methylsulfonylmethane (MSM) and the pharmaceutically active agent is dissolved therein or adheringly bonded thereto.

20. The method according to claim 19 wherein the carrier consists of at least 95% by weight of MSM.

21. The method according to claim 20 wherein the mixture is formed into granules.

22. The method according to claim 20 wherein the mixture is formed into a free-flowing powder.

23. The method according to claim 20 wherein the mixture is formed into granules.

24. The method according to claim 20 in the form of granules or a free-flowing powder, which is thereafter compressed into tablets.

25. The method according to claim 19, wherein the carrier comprises up to 5% by weight thereof of at least one colloidal or fumed silica, calcium carbonate and calcium mono-, di- or triphosphate.

26. In a pharmaceutical formulation method for producing a solid pharmaceutical composition adapted for oral ingestion which comprises the step of forming an intimate physical mixture of at least one pharmaceutically systemically active agent which is storage unstable in the presence of moisture and a pharmaceutically acceptable carrier therefor, into tablets, granules or a free-flowing powder, the improvement wherein the mixture is substantially anhydrous, the pharmaceutically active agent is in solid particulate form and the MSM is mixed therewith by condensing vapors thereof onto a moving bed of the pharmaceutically active agent.

27. The method according to claim 26 conducted at reduced pressure.

28. In a composition adapted for oral ingestion in the form of compressed units or a free-flowing powder and consisting essentially of an intimate physical mixture of at least one dietary component and a pharmaceutically acceptable carrier therefor, the improvement wherein the mixture is substantially anhydrous, the carrier consists essentially of methylsulfonylmethane and the agent is dissolved in the MSM or adheringly bonded to the surface of particles of the MSM.

* * * * *